United States Patent [19]
Joshi

[11] Patent Number: 5,932,204
[45] Date of Patent: Aug. 3, 1999

[54] CONTROLLED RELEASE OF SUBSTANCES

[75] Inventor: Ashok V. Joshi, Salt Lake City, Utah

[73] Assignee: Ceramatec, Inc., Salt Lake City, Utah

[21] Appl. No.: 08/880,124

[22] Filed: Jun. 20, 1997

Related U.S. Application Data

[63] Continuation-in-part of application No. 08/686,730, Jul. 26, 1996.

[51] Int. Cl.$^6$ .................................................. A61L 9/015
[52] U.S. Cl. .......................... 424/76.1; 424/405; 424/473
[58] Field of Search ................................. 424/76.1, 405, 424/473; 239/56

[56] References Cited

U.S. PATENT DOCUMENTS

| | | | |
|---|---|---|---|
| 2,740,662 | 4/1956 | Scott | 299/24 |
| 3,685,734 | 8/1972 | Paciorek et al. | 239/56 |
| 3,687,114 | 8/1972 | Berkstresser | 119/106 |
| 3,731,414 | 5/1973 | Murphy et al. | 40/301 |
| 4,023,532 | 5/1977 | Goodwin | 119/156 |
| 4,081,501 | 3/1978 | Muther | 264/89 |
| 4,145,001 | 3/1979 | Weyenberg et al. | 239/56 |
| 4,254,910 | 3/1981 | Martin | 239/60 |
| 4,428,327 | 1/1984 | Steckel | 119/156 |
| 4,506,630 | 3/1985 | Hair | 119/156 |
| 4,562,794 | 1/1986 | Speckman | 119/156 |
| 4,697,549 | 10/1987 | Hair | 119/156 |
| 4,721,064 | 1/1988 | Denk et al. | 119/156 |
| 4,753,389 | 6/1988 | Davis | 239/6 |
| 4,849,606 | 7/1989 | Martens, III et al. | 219/271 |
| 4,948,047 | 8/1990 | Zembrodt | 239/34 |
| 5,007,529 | 4/1991 | Spector | 206/0.5 |
| 5,016,369 | 5/1991 | Parry | 40/301 |
| 5,074,252 | 12/1991 | Morgan, Jr. | 119/156 |
| 5,077,102 | 12/1991 | Chong | 428/24 |
| 5,242,111 | 9/1993 | Nakoneczny et al. | 239/47 |

(List continued on next page.)

OTHER PUBLICATIONS

Eury et al., Abstract, "Blocked polymeric particles having internal pore networks for delivering active substances to selected environments", U.S. Patent No. 5,316,774, May 31, 1994, 2 pages.

Williford et al., Abstract, "Methods and compositions for flavoring orally–delivered products", U.S. Patent No. 5,458,890, Oct. 17, 1995, 2 pages.

*Primary Examiner*—Thurman K. Page
*Assistant Examiner*—Kathryne E. Shelborne
*Attorney, Agent, or Firm*—Factor and Shaftal, LLC

[57] ABSTRACT

A gravity force driven device and associated methods for the sustained release of a fluid such as a volatile substance into a local environment. The device includes a housing having a lumen and a first open end, at least one porous plug permeable to volatilized substance positioned within the housing's first open end and partially occupying the lumen thereby, a reservoir, defined by the lumen and porous plug, and a quantity of the fluid contained within the reservoir. In use, the device is oriented so that the substance contained within the reservoir is in constant fluid communication with the porous plug. The device may further include an inlet port for refilling the device with the substance in fluid communication with the reservoir, and, for home use, may have an ornamental piece associated with (e.g. affixed to) the device. The device may also use an electrochemical gas generating cell to assist the gravity-driven dispersal. In certain embodiments, the device will be associated with, or further include, a heating element for volatilizing the substance. In one embodiment, the device is used to deliver a beneficial agent to the skin of an animal such as a mammal. The invention also includes associated methods for using the device. The delivery devices of the instant invention are rugged and may be mass-produced at a relatively low cost. Volatile substances which can be dispensed include fragrances, perfumes, volatile insecticides, pest repellent fluids, and volatile medicament fluid compounds.

31 Claims, 4 Drawing Sheets

U.S. PATENT DOCUMENTS

| | | | |
|---|---|---|---|
| 5,266,543 | 11/1993 | Matsumoto et al. | 502/66 |
| 5,291,742 | 3/1994 | Kawatani et al. | 62/78 |
| 5,357,700 | 10/1994 | Schulte | 40/301 |
| 5,361,522 | 11/1994 | Green | 40/152.1 |
| 5,372,303 | 12/1994 | Paul | 239/56 |
| 5,373,581 | 12/1994 | Smith | 392/390 |
| 5,399,404 | 3/1995 | Laughlin et al. | 428/40 |
| 5,431,859 | 7/1995 | Tobin | 261/52 |
| 5,437,410 | 8/1995 | Babasade | 239/55 |
| 5,439,100 | 8/1995 | Gordon et al. | 206/0.5 |
| 5,443,461 | 8/1995 | Atkinson et al. | 424/473 |
| 5,447,693 | 9/1995 | Ohta et al. | 422/122 |
| 5,462,741 | 10/1995 | Carr et al. | 424/438 |
| 5,468,447 | 11/1995 | Bermas | 422/5 |
| 5,478,505 | 12/1995 | McElfresh et al. | 261/30 |
| 5,487,869 | 1/1996 | Retallick | 422/22 |
| 5,705,191 | 1/1998 | Price et al. | 424/473 |
| 5,714,160 | 2/1998 | Magruder et al. | 424/438 |

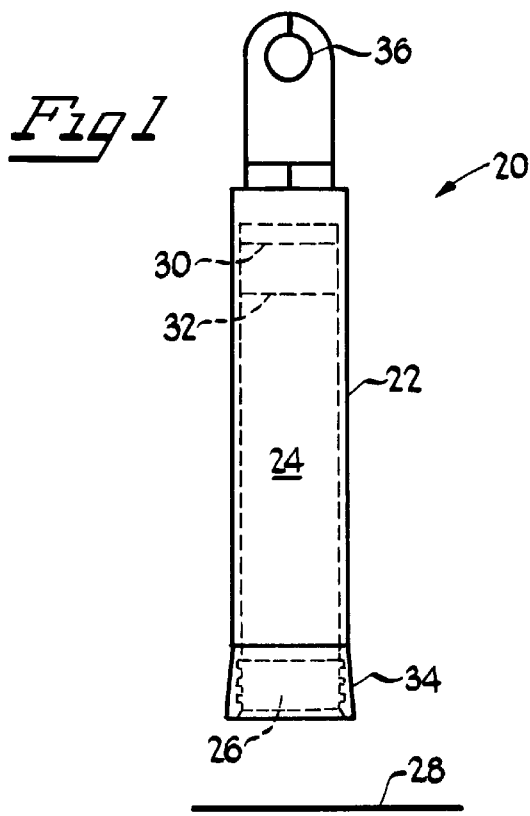
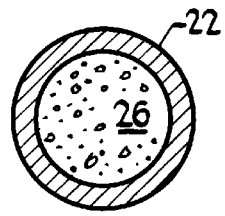
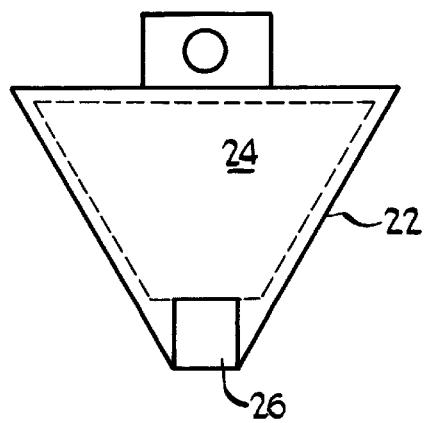
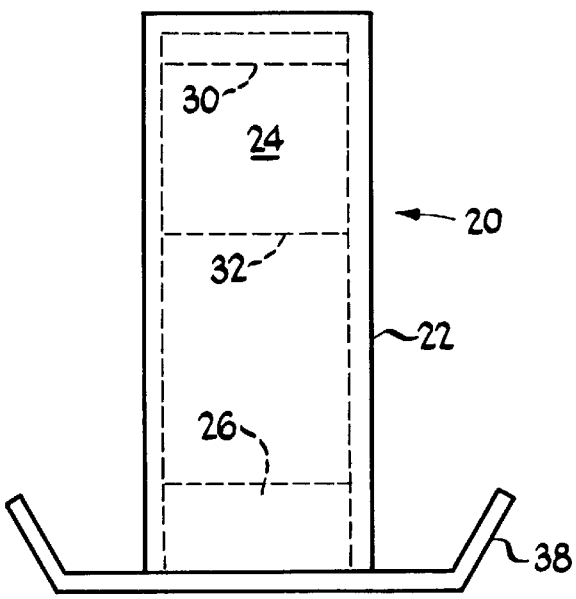

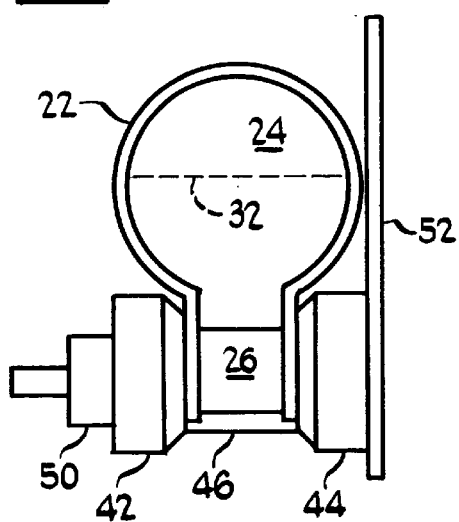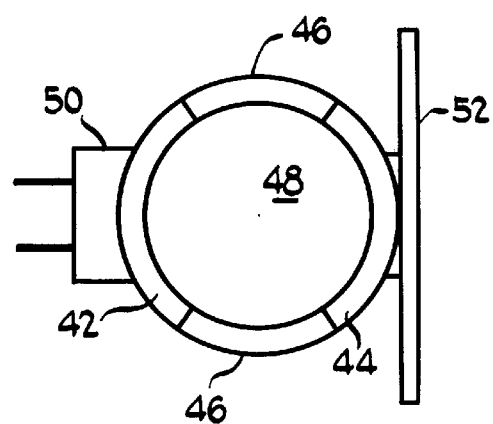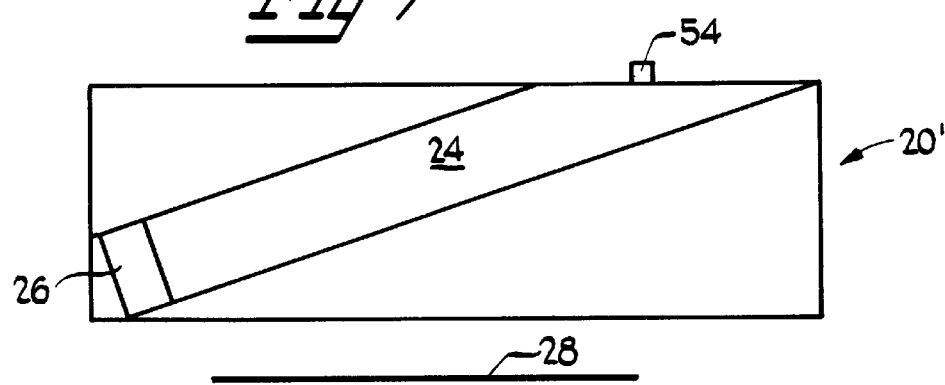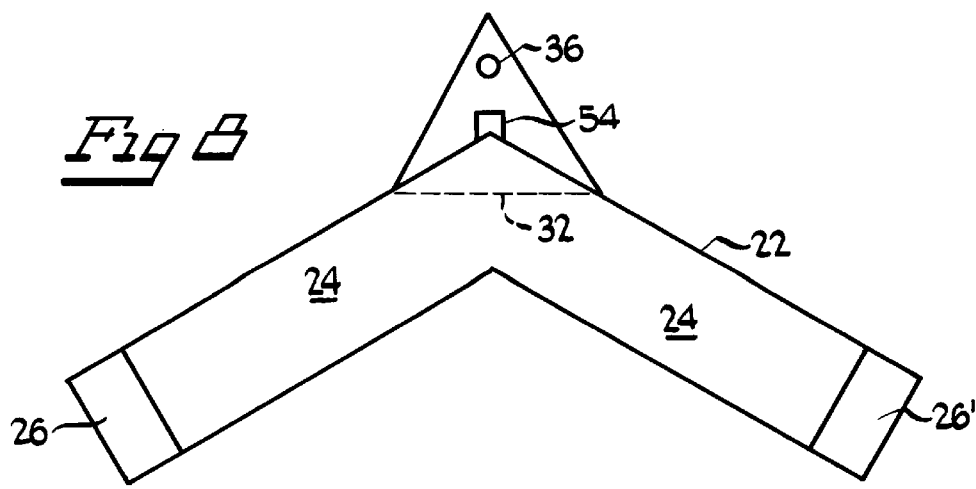

1

CONTROLLED RELEASE OF SUBSTANCES

RELATED APPLICATION

This application is a continuation-in-part of U.S. patent application Ser. No. 08/686,730 filed on Jul. 26, 1996.

TECHNICAL FIELD

This invention generally relates to devices and associated methods useful for the controlled release of volatile substances. More specifically, the invention relates to a device useful for the controlled and prolonged release of volatile or other fluids such as perfumes, fragrances, pesticides, pest repellents, and other substances.

BACKGROUND

Patents exist describing devices for dispensing volatile substances in the air through diffusion phenomenon. For instance, U.S. Pat. No. 3,685,734 to Paciorek et al. (Aug. 22, 1972) describes a multi-layer polymeric controlled fragrance-release device. The Paciorek et al. device uses a separate flexible sheet to cover a fragrance bearing middle sheet of plastisol. This cover sheet has very low vapor transmission, but upon its removal, fragrance is reportedly immediately detectable and is gradually released from the device.

U.S. Pat. No. 4,145,001 to Weyenberg et al. (Mar. 20, 1979) also describes a multi-layer polymeric package for the controlled release of a volatile substance (e.g. deodorizer) sandwiched between layers. The outer layers of the laminate are impermeable to the volatile substance and its vapors and thus prevent escape of vapors as long as the package is sealed. Upon opening the package, delamination occurs at the interface between two selected layers such that the volatile substance is covered only on one side by a layer which is permeable to vapors thereby allowing controlled release of volatile materials.

U.S. Pat. No. 5,242,111 to Nakoneczny et al. (Sep. 7, 1993) describes a liquid dispensing device which consists of a sealed flexible bag or pouch containing the supply of the active volatile fluid, a wick located inside a tubular chamber and an emanator which diffuses the liquid. U.S. Pat. No. 5,437,410 to Babasade (Aug. 1, 1995) also describes the use of a wick to dispense a fragrance.

U.S. Pat. No. 4,849,606 to Martens, III et al. (Jul. 18, 1989) describes a tamper-resistant plastic container which has a multi-layered flexible seal over its open end. The container has at least one free standing grid which prevents downward pressure or squeezing of the container's seal which might rupture the seal or result in a leakage of the fluid.

U.S. Pat. No. 5,478,505 to McElfresh et al. (Dec. 26, 1995) describes a device for dispensing fragrance into the atmosphere. This device has an attachment clip and uses low density polyethylene as a diffusion membrane. This membrane is sealed to a plastic container similarly to U.S. Pat. No. 4,849,606 to Martens, III et al.

Similar devices for dispensing pesticides or pest repellants are believed to exist.

Unfortunately, in use, the prior art devices do not generally display a constant release rate from the device over time. At first, the release rate is adequate and steady, but after time, the release rate diminishes, which is not suitable for certain applications wherein a constant release rate over time is desired. Also, the fluid utilization with the prior art devices is generally less than adequate in that even though the device is used up from a practical point of view, fluid still remains in the device which is unutilized, and needs to be disposed of properly.

SUMMARY OF THE INVENTION

The invention includes a gravity-driven device for the sustained and efficient release of a fluid into a local environment such as air or a contact surface.

The invention thus includes a device for releasing a fluid, especially one capable of volatilization. The inventive device includes (a) a housing having a lumen and at least one open end, (b) at least one porous plug permeable to the fluid positioned within each open end and thus partially occupying the lumen, (c) a reservoir, defined by the lumen and porous plug, and (d) a quantity of the fluid contained within the reservoir. In use, the device is oriented so that the fluid contained within the reservoir will be driven by gravity to be in constant fluid communication with the porous plug. As long as the fluid in the container is in fluid communication with the porous plug, the device will allow the fluid to release (e.g. vaporize) from an exterior surface of the porous plug into, for example, the local atmosphere at a sustained rate. The device may further include an inlet port for refilling the device with the fluid in fluid communication with the reservoir, and, for residential use, may have an ornamental piece associated with (e.g. affixed to) the device for safety and aesthetic reasons.

In certain embodiments, the device will be associated with, or further include, a heating element for volatilizing the substance and/or an electrochemical cell for assisting the gravity driven device. The invention also includes associated methods for using the device.

In another embodiment, the device is associated with a relatively large surface area emanator in fluid contact with the porous plug to increase the intensity of release.

Although the device is generally described with regard to the release and vaporization of a fluidic substance into the local atmosphere, variations of the device can be used to release a liquid onto a surface to be treated such as releasing an oil-based pest repellant solution onto the skin of an animal such as cattle or other livestock (e.g., the device can be used as a livestock ear tag wherein an exposed surface of the porous plug contacts the, for example, mammal's skin, releasing liquid from the device onto the skin surface being contacted).

Devices according to the instant invention are rugged and may be mass-produced at a relatively low cost. Beneficial agents which can be dispensed include fragrances, perfumes, volatile insecticides, pesticides, pest repellent fluids, volatile medicaments, and mixtures thereof. Fluid disposal problems associated with the prior art devices are avoided by nearly complete utilization of the fluid in the reservoir.

BRIEF DESCRIPTION OF THE DRAWINGS

In the drawings, which depict presently preferred embodiments of the invention and in which like reference numerals refer to like parts in different views:

FIG. 1 depicts a side view of a device according to the invention.

FIG. 2 depicts a bottom view of the device of the preceding figure.

FIG. 3 depicts an alternative embodiment of the invention.

FIG. 4 depicts an alternative embodiment of the invention wherein the device is associated with an "emanator dish" to enhance volatilization or evaporation of volatile substance into the atmosphere.

FIG. 5 depicts an alternative embodiment of the invention, wherein the plug and the fluid contained within the plug are heated before delivery to enhance the evaporation of the fluid.

FIG. 6 depicts a top view of a member for heating a device as shown in the preceding figure.

FIG. 7 depicts an alternative embodiment of the invention wherein the lumen of the device is oriented within the device to take advantage of the force of gravity to disperse the volatile fluid.

FIG. 8 depicts another alternative embodiment of the invention wherein the device uses two porous plugs to disperse the fluid into the local atmosphere.

BEST MODE OF THE INVENTION

Figure 9:
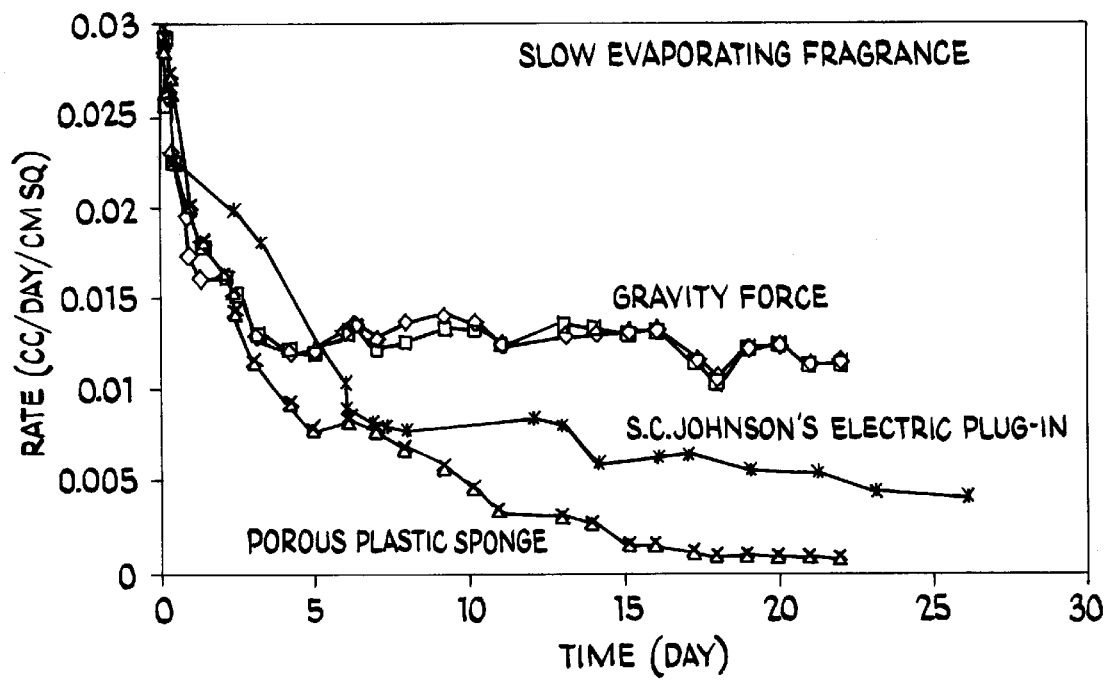
FIG. 9 is a graph depicting the rate of release versus time for a device according to the invention and that of another device.

For the purposes of illustration of the present invention, an embodiment of the sustained release device is shown in FIG. 1. The depicted device, generally 20, has a open cylindrical housing 22 (the interior lumen of which is shown by construction lines in FIG. 1) which defines a reservoir 24 for containing a quantity of the substance which is volatile or volatizable. Positioned within the open end of the housing is a porous plug 26.

The housing 22 is substantially impermeable to the substance contained within the reservoir, but, in one particularly embodiment, may be slightly permeable to the gas which makes up the local atmosphere surrounding the housing (e.g., air). Typical materials from which the housing is made include metals, plastics (e.g., polyethylene), dense ceramics, glass, or mixtures thereof.

The substance to be delivered by the device can be a beneficial agent in and of itself, or it can be a beneficial agent dissolved in a solvent such as water, oil, ethanol and like fluids.

The lumen of the housing 22 generally corresponds to the reservoir and the space occupied by the porous plug 26 within the cylinder. In use, the lumen of the device 22 is oriented so that the volatile substance contained within the reservoir 24 is driven by gravity through the porous plug 26 (for example, as depicted in FIG. 1, the device 22 is oriented in a plane generally perpendicular to level (or earth) 28. This involves placing the device in such an orientation that the porous plug is oriented downwards so that fluid is drawn, by gravity, into contact with the interior surface of the porous plug 26 (that portion of the porous plug exposed to the fluid in the reservoir) thus allowing the fluid to pass through the porous plug to an exterior, exposed surface of the porous plug 26. As gravity drives fluid out of the porous plug 26, the level of the fluid within the reservoir decreases from an initial level (shown by construction line 30) to a lower level (shown by construction line 32) with respect to the earth 28. The fluidic substance is replaced by gas which passes through the porous plug in a direction opposite that of the flow of the volatile substance through the porous plug.

The porous plug 26 is preferably made of a material such as porous plastic, porous ceramic, porous metals, porous glass, cellulose, cellulose derivatives, and mixtures thereof. The porous plug 26 has the appropriate size, shape, porosity and surface tension to retain itself and the fluid within the housing 22 without allowing fluid to drip from the device 20. The porous plug in this regard is different than classical wick or "wicking" in that it does not display significant capillary action, but still allows fluid transfer from the reservoir to the exposed surface of the porous plug, and exposure of the fluid on the exposed surface for evaporation or contact application.

The surface area of the porous plug 26 exposed to the atmosphere (FIG. 2) and the size and thickness of the housing 22 will be chosen taking into consideration the amount of substance to be released into the local environment, the type of release (e.g. contact application or evaporation) the length of time over which release is desired, and the environment into which the substance is to be released. The rate of release from the porous plug will generally depend on the pore size of the porous plug, and the porous plug's length and diameter, as well as the surface tension and vapor pressure of the substance contained within the reservoir at operating temperature.

The device may be actuated by removing a sealing member 34 (e.g. plasticized metal foil or metallized plastic membrane) which covers the end of the device having the porous plug 26 and orienting the device (e.g. by hanging it from a cord or hook strung through aperture 36) so that the porous plug becomes saturated with liquid from the reservoir 24. In devices which utilize an electrochemical gas generating cell, the cell too may be activated.

Figure 10:
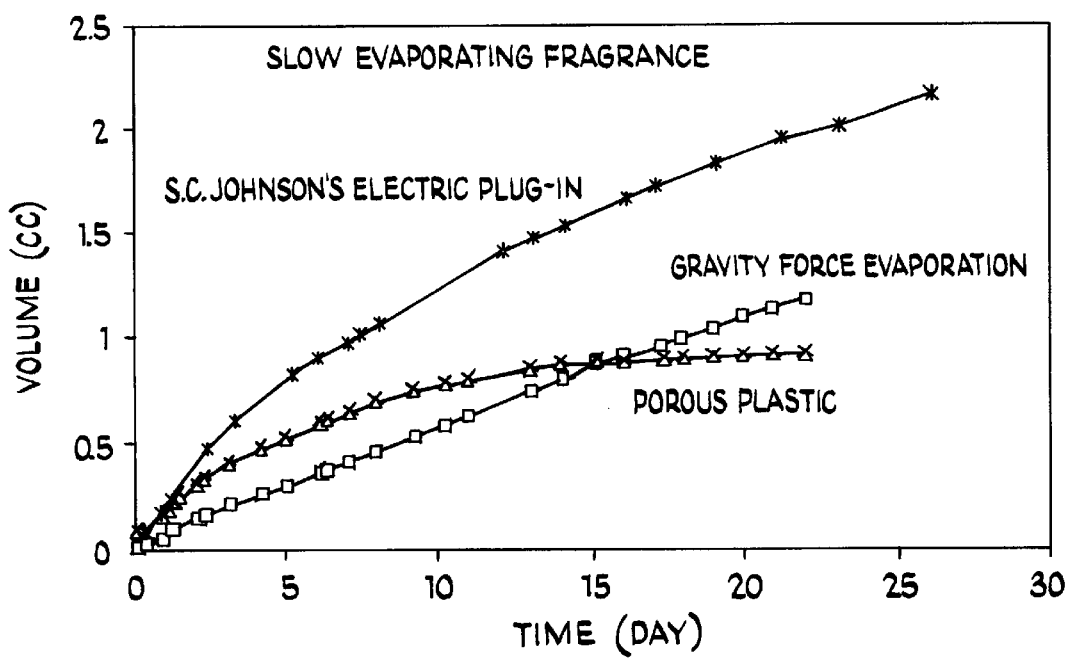
FIG. 10 is a graph depicting the volume of volatile substance released over time for a device according to the invention and that of other devices.

The fluid releases from the exposed surface of the porous plug 26 by, for example, evaporation to the local atmosphere or surface contact with a surface to which the fluid is to be applied. The saturated porous plug 26 acts a saturated sponge, and the rate of release from the device 20 is constant. The rate of release of fluid from the device 20 depends on the amount of surface area exposed to the atmosphere or surface to which fluid is to be applied. As shown in FIGS. 9 & 10 which depict the release characteristics of a volatile fluid from a device into the local atmosphere over time, after stabilizing, a nearly flat line release rate continues until the device is empty. In contrast, other devices display a continually decreasing release rate over time.

FIG. 3 depicts an alternative embodiment of the invention wherein the device has an inverted triangular shape (in cross section). In this embodiment, the effects of the pressure caused by the liquid column of substance are minimized by the triangular shape of the container. Due to this shape, the force on the fluid and plug remain relatively constant during use since the height variations in the fluid level which occur over time during use of the device are minimized by the shape of the reservoir.

FIG. 4 depicts an alternative embodiment of the invention wherein the device is associated with an "emanator dish" 38. This emanator dish 38 is preferably lined with (or completely made of) a porous material which is in fluid communication with the porous plug 26 and the local atmosphere. Such a structure 38 helps to diffuse the material into the atmosphere at an accelerated rate, and may be used to structurally support the device and properly orient it with respect to level when it is placed on a flat surface such as a table or floor. The dish 38 may be associated with a decorative element.

Alternatively, rather than using an emanator dish, a wick (preferably a large surface area wick) or other equivalent device can be placed in fluid communication with the exterior portion of the porous plug so as to enhance the evaporation rate from the device without interfering with the beneficial effects of using gravity to drive the device.

FIGS. 5 and 6 depict another alternative embodiment of the invention wherein the fluid contained within the reservoir is heated before volatilization of the substance to disperse it into the atmosphere. In this embodiment, a structure 40 for heating a device according to the invention includes heating elements 42, 44 (e.g. electrically operated resistive heating elements) which, together with a structural member 46, form a receptacle 48 for a portion of the device, preferably a portion of the device which includes the porous plug 26. The heating structure 40 also includes a standard electrical wall socket pronged unit 50 for placement in a wall socket (not shown). Standard electrical circuitry, well known to those of skill in the art, for heating the device within the receptacle 48 is incorporated into the heating structure. The depicted device includes an ornamental facade 52 for covering up the device from view, and protecting it from accidental breakage.

As can be seen by comparing the device depicted in FIG. 1 or FIG. 3 with that depicted in FIGS. 5 and 6, a device according to the invention can made be in various shapes and sizes. For instance, as depicted in FIG. 7, the device 20' can be block shaped, wherein the reservoir is oriented within the device 20' to take advantage of gravity for dispensing the fluid from the reservoir 24 contained within the device 20'. The device 20' depicted in FIG. 7 has an inlet port 54 for refilling the reservoir as needed.

Likewise, FIG. 8 depicts still another alternative embodiment of the invention wherein the device uses two porous plugs 26, 26' to disperse the fluid into the local atmosphere from the reservoir 24 contained within the cylindrical housing. Of course a plurality of such plugs could be used (e.g., if the device were in an octopus-type arrangement wherein the body was the reservoir, and the downward extending arms were the tubes feeding porous plugs placed at the end of each tube).

Figure 13:
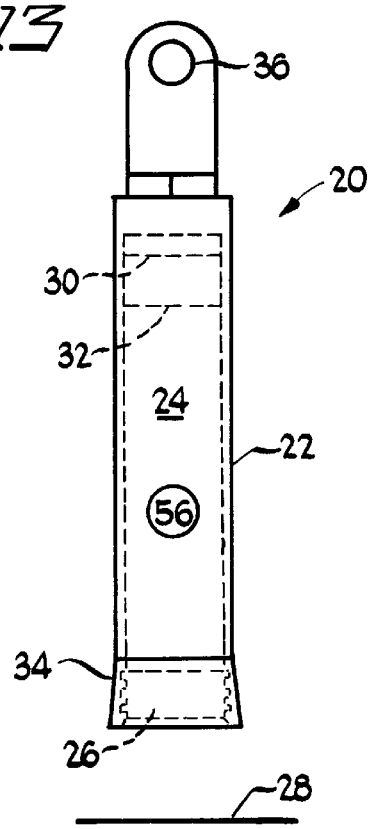
FIG. 13 depicts an alternative embodiment of the invention wherein the device is associated with an electrochemical gas generating cell to assist gravity in dispensing the fluid.

FIG. 13 depicts an alternative embodiment of the invention wherein the device is associated with an electrochemical gas generating cell to assist gravity in dispensing the fluid. The device, generally 20, is similar to the previously described devices in having a housing 22, reservoir 24, porous plug 26, and means for orienting the reservoir so as to utilize gravity to drive the fluid to contact the porous plug 26, but also includes an electrochemical gas generating cell 56. Upon actuation, the gas generating cell is used to assist the effects of gravity is dispersing the substance. Such a pump is preferably, a hydrogen or oxygen generating cell. The gas cell may be a gas releasing electrochemical cell such as those disclosed in U.S. Pat. Nos. 5,427,870 (Jun. 27, 1995) and 5,454,922 (Oct. 3, 1995) to Joshi et al., the contents of the entirety of both of which are incorporated by this reference.

After being apprised of the invention, one of skill in the art would be able to make a device according to the invention. For instance, a housing can be blow molded, thermally formed, or injection molded from plastic, and the porous plug can be formed of polymers, metals, ceramics, glasses, cellulose or mixtures thereof in a shape appropriate to fit within the housing.

Devices according to the invention have certain advantages over other devices. For instance, the devices can have a more linear release, a higher rate of release, a large amount of fragrance released through a small area plug at a constant rate, prior art wick-based systems are limited by height, while there is no such limitation on the use of gravity force, and the constant gravity force results in a constant release.

Various modifications can be made to the invention. For instance, absorbent material such as glass wool, polymer wool, non-woven polymer, cotton-based absorbent materials, or mixtures thereof can be contained within the reservoir. Alternatively, the substance can be admixed with an appropriate gelling agent.

Furthermore, the device can include means for adjusting the rate of release of fluid from the device by, for example, moving the releasing portion of the device from one associated emanating structure to another associated emanating structure having a greater or lesser surface area for volatilizing the fluid to increase or decrease the rate of release from the device respectively. Alternatively, the device could further include a cover for covering at least a portion of the exteriorly exposed surface of the porous plug which cover prevents release of fluid from the porous plug.

The invention is further explained by the following illustrative examples.

EXAMPLES

Example I

A device was fabricated as shown in FIG. 1. The plastic container was made out of DELRIN™ (acetal resin from DUPONT), and has an internal diameter of 0.570" and a length of about 2.7". The plastic container is filled with a slowly evaporative fragrant liquid obtained from IFF. After filling the container with about 7.6 cc of fragrance, a porous plug (made out of polyethylene plastic) was inserted into the open end of the container. The plug was obtained from Interflow Technologies and had dimensions of 0.610" diameter by 0.500" length. The plug was inserted with an interference fit in the container. The container was then hung as shown in FIG. 1 so that the porous plug faced downwards (toward the earth). The porous plug was quickly filled and saturated with fragrant liquid. The fragrant liquid started evaporating into the atmosphere.

Example II

Another porous plastic plug filled completely with the same slowly evaporative fragrant liquid as EXAMPLE I was hung beside the device of EXAMPLE I to carry out a comparative study of the two systems. Evaporation of fragrant liquid from the saturated porous plug drove this second system. A third device (i.e. a GLADE™ electrical plug in device commercially available from S. C. Johnson) was also analyzed. The release rate data of the three systems is depicted in FIG. 9. As shown in FIG. 9, all of the systems being compared initially exhibited a decline in the rate of release, but after three days or so, the device of EXAMPLE I stabilized, and the rate became substantially constant while the saturated porous plastic sponge continued to decline in rate of evaporation.

The data obtained in this experiment shows that using gravity to drive fragrance release systems is an advantageous method for delivering large amounts of fragrance at a controlled and constant rate.

Example III

Figure 11:
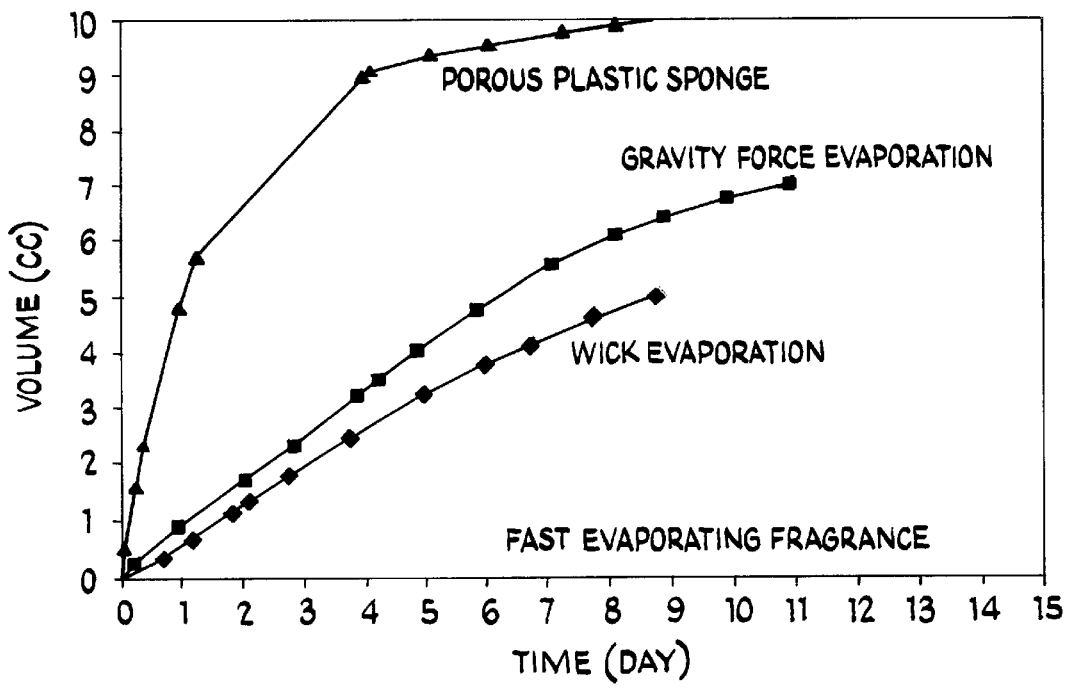
FIG. 11 is a graph depicting the rate of volume of volatile substance released from various devices versus time (using a fast evaporating fragrance).
Figure 12:
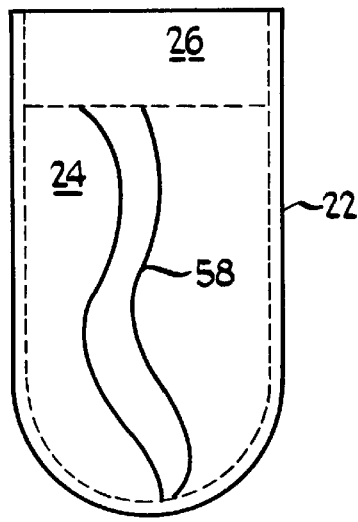
FIG. 12 depicts a device made for comparative EXAMPLE IV.

In this example, the evaporation of a highly volatile fragrant liquid from three different devices (i.e. a gravity force evaporator per EXAMPLE I, a wick-type evaporator, and a porous plastic sponge as per EXAMPLE II) was studied. The results from this study are depicted in FIG. 11. The porous plastic sponge was a sponge having 35 sq. cm. gross surface area. It contained about 11 g of fragrance. The gravity force evaporator is as described in EXAMPLE I. The wick-type device used the same plastic porous plug in conjunction with the wick 58 as shown in FIG. 12. The wick was made of a highly absorbent wick material made of polypropylene fibers. Both the wick-type device and the gravity force device contained 7.6 cc of fragrance, while the porous plastic sponge contained 11 g. of fragrance. FIG. 11 shows that the gravity force evaporator of EXAMPLE II dispersed fragrance much more linearly than the other devices. The gravity force evaporator disperses at the highest rate of fragrance per square centimeter of area than any other device. The gravity force evaporator was also the most economical of the devices studied, and exhibits a significantly constant release of volatile substance.

Example IV

In this example, the release characteristics of a gravity force device (i.e. a device as per EXAMPLE I associated with a wick) were compared with a wick-type device. The wick-type device was 14 inches long. The wick was 13 inches long. The wick-type device could not draw all the fragrant liquid out of the reservoir after a day, and after a couple of days, a certain reservoir level in the wick was reached, the device stopped releasing fragrant fluid. In contrast, the gravity force wick-type device continued releasing fluid until the reservoir was empty.

Example V

The release characteristics of a gravity force driven device having a porous plug with a dispensing surface for non-volatile fluid application to a surface local environment was observed and measured. A device such as that depicted in FIG. 1 was filled with isopropyl myristate. The porous plug was made of polyethylene (available from Interflow Technologies). The exteriorly exposed surface of the porous plug was contacted with absorbent paper every minute for fifty minutes, and was weighed every five minutes, from which it was determined that about ten (10) milligrams of fluid was being applied to the paper per five (5) applications. In total, about 100 mg of fluid was transferred after 50 applications.

Although the invention has been described with regard to certain preferred embodiments and examples, the scope of the invention is to be defined by the appended claims.

What is claimed is:

1. A device for releasing a fluid into a local environment, said device comprising:
   a housing having a lumen and a first open end;
   a porous plug having a surface exposed to the local environment, said porous plug positioned within the housing's first open end and partially occupying said lumen thereby, said porous plug permeable to a fluid;
   a reservoir having a volume defined by the lumen and porous plug, said reservoir orientable to deliver fluid to the porous plug by the force of gravity;
   a quantity of a fluid contained within said reservoir; and
   means for orienting the device so that gravity delivers substantially all of a fluid from the reservoir to the porous plug's exposed surface;
   an electrically operated heating element for volatilizing a fluid, wherein the heating element is directly associated with the porous plug.

2. The device of claim 1 further comprising:
   an inlet port for refilling the device with a fluid, said inlet port in fluid communication with the reservoir.

3. The device of claim 1 further comprising an ornamental piece associated with said device.

4. The device of claim 2 wherein the housing has a plurality of open ends each having a porous plug associated therewith.

5. A device for releasing a fluid into a local environment, said device comprising:
   a housing having a lumen and a first open end;
   a porous plug having a surface exposed to the local environment, said porous plug positioned within the housing's first open end and partially occupying said lumen thereby, said porous plug permeable to a fluid;
   a reservoir having a volume defined by the lumen and porous plug, said reservoir orientable to deliver fluid to the porous plug by the force of gravity;
   a quantity of a fluid contained within said reservoir; and
   means for orienting the device so that gravity delivers substantially all of a fluid from the reservoir to the porous plug's exposed surface; and
   the associated reservoir is in fluid communication with an electrochemical gas generating cell.

6. The device of claim 1 wherein the porous plug is made of a material selected from the group of porous materials consisting of porous plastic, porous ceramic, porous metals, porous glass, cellulose, cellulose derivatives, and mixtures thereof.

7. The device of claim 1 further comprising a fluid-tight sealing tape membrane covering said porous plug thus preventing fluid communication between the porous plug and the local environment.

8. The device of claim 9 wherein the fluid-tight sealing tape membrane is made of a metallic or non-porous polymeric material or a combination thereof.

9. The device of claim 1 wherein the porous plug is in fluid communication with an emanating structure to enhance the evaporation rate from the emanating structure.

10. The device of claim 9 wherein the device further comprises means for adjusting the rate of release of substance from the device.

11. The device of claim 1 wherein the housing is permeable to air, but not permeable to a volatilized fluid.

12. A method of dispersing a fluid capable of volatilization into a local atmosphere, the method comprising:
   containing a volatile fluid within the device of claim 9;
   removing said fluid-tight membrane from the device; and
   thus dispersing the fluid into the atmosphere.

13. A method according to claim 12 further comprising heating a fluid.

14. A method according to claim 13 wherein a fluid is heated at the porous plug of the device.

15. A method according to claim 12 wherein the porous plug is oriented downwards within the device in such a manner that gravity assists in saturating the porous plug with volatile fluid so that the quantity of fluid contained within the reservoir is dispersed into the atmosphere.

16. A method of dispersing a fluid capable of volatilization into a local atmosphere, the method comprising:

containing a volatile fluid within the device of claim 5;

actuating said gas-generating cell and orienting the device so that the porous plug is directed downwards; and thus dispersing a fluid into the atmosphere.

17. A method of applying a beneficial agent to the skin of an animal, said method comprising:

applying to the animal's ear a device for releasing a fluid into a local environment, said device comprising:

a housing having a lumen and a first open end;

a porous plug positioned within the housing's first open end and partially occupying said lumen thereby, said porous plug permeable to said fluid;

a reservoir having a volume defined by the lumen and porous plug, said reservoir orientable to deliver fluid to the porous plug by the force of gravity;

a quantity of a fluid comprising the beneficial agent contained within said reservoir; and means for orienting the device so that gravity delivers fluid from the reservoir to the porous plug, said device being of a length sufficient that an exteriorly exposed surface of a porous plug of said device occasionally contacts the animal's skin where beneficial agent is to be applied; and orienting said device so that a fluid is directed by gravity to the porous plug.

18. A device for releasing a fluid into a local environment, said device comprising:

a housing having a lumen and a first open end;

a porous plug having a surface exposed to the local environment, said porous plug positioned within the housing's first open end and partially occupying said lumen thereby, said porous plug permeable to a fluid;

a reservoir having a volume defined by the lumen and porous plug, said reservoir orientable to deliver fluid to the porous plug by the force of gravity;

a quantity of a fluid contained within said reservoir; and wherein the housing has a plurality of open ends each having a porous plug associated therewith.

19. The device of claim 5 further comprising:

an inlet port in fluid communication with the reservoir.

20. The device of claim 5 further comprising an ornamental piece associated with said device.

21. The device of claim 5 further comprising a heating element for volatilizing a fluid, and wherein the heating element is associated with the porous plug.

22. The device of claim 5 wherein the porous plug is made of a material selected from the group of porous materials consisting of porous plastic, porous ceramic, porous metals, porous glass, cellulose, cellulose derivatives, and mixtures thereof.

23. The device of claim 5 further comprising a fluid-tight sealing tape membrane covering said porous plug thus preventing fluid communication between the porous plug and the local environment.

24. The device of claim 23 wherein the fluid-tight sealing tape membrane is made of a metallic or non-porous polymeric material or a combination thereof.

25. The device of claim 5 wherein the porous plug is in fluid communication with an emanating structure to enhance the evaporation rate from the emanating structure.

26. The device of claim 25 wherein the device further comprises means for adjusting the rate of release of substance from the device.

27. The device of claim 5 wherein the housing is permeable to air, but not permeable to a volatilized fluid.

28. A method of dispersing a fluid capable of volatilization into a local atmosphere, the method comprising:

containing a volatile fluid within the device of claim 23;

removing said fluid-tight membrane from the device; and thus dispersing a fluid into the atmosphere.

29. A method according to claim 28 further comprising heating a fluid at the porous plug of the device.

30. A method according to claim 28 wherein the porous plug is oriented downwards within the device in such a manner that gravity assists in saturating the porous plug with volatile fluid so that the quantity of fluid contained within the reservoir is dispersed into the atmosphere.

31. The device of claim 1 wherein the associated reservoir is in fluid communication with an electrochemical gas generating cell.

* * * * *